(12) United States Patent
Kobayashi et al.

(10) Patent No.: US 11,453,899 B2
(45) Date of Patent: *Sep. 27, 2022

(54) METHOD OF PRODUCING PROTEIN (71) Applicant: Toray Industries, Inc., Tokyo (JP)

(72) Inventors: Koji Kobayashi, Kamakura (JP);
Shingo Hiramatsu, Kamakura (JP);
Katsushige Yamada, Kamakura (JP)

(73) Assignee: Toray Industries, Inc., Tokyo (JP)

(*) Notice: Subject to any disclaimer, the term of this patent is extended or adjusted under 35 U.S.C. 154(b) by 519 days.

This patent is subject to a terminal disclaimer.

(21) Appl. No.: 16/088,950

(22) PCT Filed: Mar. 30, 2017

(86) PCT No.: PCT/JP2017/013377
§ 371 (c)(1),
(2) Date: Sep. 27, 2018

(87) PCT Pub. No.: WO2017/170917
PCT Pub. Date: Oct. 5, 2017

(65) Prior Publication Data
US 2020/0165647 A1 May 28, 2020

(30) Foreign Application Priority Data
Mar. 31, 2016 (JP) .............................. JP2016-070584

(51) Int. Cl.
| | | |
|---|---|---|
| C12N 9/24 | (2006.01) | |
| C12N 9/42 | (2006.01) | |
| C12N 9/44 | (2006.01) | |
| C12P 19/04 | (2006.01) | |
| C12N 1/14 | (2006.01) | |
| C12N 1/38 | (2006.01) | |
| C12P 19/02 | (2006.01) | |
| C12P 19/14 | (2006.01) | |

(52) U.S. Cl.
CPC ................ *C12P 19/04* (2013.01); *C12N 1/14* (2013.01); *C12N 1/38* (2013.01); *C12N 9/248* (2013.01); *C12N 9/2437* (2013.01); *C12P 19/02* (2013.01); *C12P 19/14* (2013.01)

(58) Field of Classification Search
CPC ....... C12P 19/14; C12P 19/02; C12P 2203/00; C12P 7/00; C12N 9/248; C12N 9/2445; C12N 1/14; C12N 9/24; C12Y 302/01021; C12Y 302/01004; C12Y 302/01; C12Y 302/01032
USPC ........ 435/254.6, 69.1, 252.2, 200, 203, 209, 435/121
See application file for complete search history.

(56) References Cited

U.S. PATENT DOCUMENTS

2010/0124769 A1 5/2010 Brown et al.
2013/0337510 A1 12/2013 Brown et al.
2016/0010130 A1 1/2016 Yamada et al.
2016/0040203 A1 2/2016 St. John et al.
2016/0208300 A1 7/2016 Yamada et al.

FOREIGN PATENT DOCUMENTS

| | | |
|---|---|---|
| EP | 3 088 530 A1 | 11/2016 |
| EP | 3 43 8 263 A1 | 2/2019 |
| EP | 3 438 272 A1 | 2/2019 |
| JP | 07-031467 A | 2/1995 |
| JP | 11-507837 A | 7/1999 |
| JP | 2009-171885 A | 8/2009 |
| JP | 2013-515482 A | 5/2013 |
| JP | 2013-533751 A | 8/2013 |
| JP | 2014-150745 A | 8/2014 |
| WO | 97/00964 A1 | 1/1997 |
| WO | 2011/038019 A2 | 3/2011 |
| WO | 2011/079048 A9 | 8/2011 |
| WO | 2012/027580 A1 | 3/2012 |
| WO | 2014/129489 A1 | 8/2014 |
| WO | 2014/208493 A1 | 12/2014 |
| WO | 2015/025927 A1 | 2/2015 |
| WO | 2015/099109 A1 | 7/2015 |
| WO | 2015/187935 A1 | 12/2015 |
| WO | 2016/068223 A1 | 5/2016 |
| WO | 2016/100825 A1 | 6/2016 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340, in IDS.*
Witkowski et al., Biochemistry 38:11643-11650, 1999.*
Kisselev L., Structure, 2002, vol. 10: 8-9.*
Qing etal Biotechnol biofuels 2011, 4, pp. 1-12.*
L.S. Mao et al., "Study on production of xylo-oligosaccharides from xylan hydrolyzed by selectively purified endo-b-xylanse," *Linchan Huaxue Yu Gongye*, vol. 26, No. 1, 2006, pp. 124-126, including an English abstract.
B.J. Gallo et al., "Cellulase production by a new mutant strain of Trichoderma reesei MCG77," *Biotechnol. Bioeng. Symp.*, vol. 8, 89, 1978, (Abstract only).

(Continued)

*Primary Examiner* — Tekchand Saidha
*Assistant Examiner* — Mohammad Y Meah
(74) *Attorney, Agent, or Firm* — DLA Piper LLP (US)

(57) ABSTRACT

A method produces a protein using a filamentous fungus, in which decrease in dissolved oxygen saturation during culture of the filamentous fungus can be suppressed even when the culture is scaled up. The method of producing a protein includes culturing a fungus belonging to the genus *Trichoderma* whose BXL1 gene was disrupted, using a biomass containing cellulose and xylan as an inducer. The use of the BXL1 gene-disrupted fungus belonging to the genus *Trichoderma* enables suppression of the decrease in dissolved oxygen saturation even when xylose and cellulose are used as inducers.

4 Claims, 1 Drawing Sheet

Specification includes a Sequence Listing.

(56) References Cited

OTHER PUBLICATIONS

A.L. Allen et al., "Cellulase production in continuous and fed-batch culture by Trichoderma reesei MCG80," *Biotechnol. Bioeng. Symp*, vol. 12, 451-459, 1982, (Abstract only).

Lehmann, L. et al., "Linking hydrolysis performance to Trichoderma reesei cellulolytic enzyme profile", *Biotechnology and Bioengineering* (Online Nov. 20, 2015), (Nov. 20, 2015), vol. 113, No. 5, pp. 1001-1010, XP002793112.

Reen, F. J. et al., "Molecular characterisation and expression analysis of the first hemicellulase gene (bxl1) encoding beta-xylosidase from the thermophilic fungus Talaromyces emersonii", *Biochemical and Biophysical Research Communications*, Elsevier, Amsterdam, NL, Jun. 6, 2003, (Jun. 6, 2003), vol. 305, No. 3, pp. 579-585, XP002685776.

La Grange, D. C. et al., "Degradation of xylan to D-xylose by recombinant *Saccharomyces cerevisiae* coexpressing the Aspergillus niger beta-xylosidase (x1nD) and the Trichoderma reesei xylanase II (xyn2) genes", *Applied and Environmental Microbiology*, American Society for Microbiology, US, Dec. 1, 2001 (Dec. 1, 2001), vol. 67, No. 12, pp. 5512-5519, XP008135576.

Drouet, P. et al., "Production of Alkyl BETA.-D-Xylosides with the Trichoderma reesei .BETA.-Xylosidase", *Annals of the New York Academy of Sciences*, Mar. 1, 1995 (Mar. 1, 1995), vol. 750, No. 1 Enzyme Engine, pp. 306-311, XP055022854.

The Extended European Search Report dated Aug. 7, 2019, of counterpart European Application No. 17775451.2.

Medve J. et al., "Ion-exchange chromatographic purification and quantitative analysis of Trichoderma reesei cellulases cellobiohydrolase I, II and endoglucanase II by fast protein liquid chromatography", *Journal of Chromatography A*, 1998, vol. 808, No. 1-2, pp. 153-165.

Chen, H. et al., "Ion-exchange chromatographic purification and quantitative analysis of Trichoderma reesei cellulases cellobiohydrolase I, II and endoglucanase II by fast protein liquid chromatography", *Biochim Biophys Acta*, May 1992, vol. 1121, No. 1-2, pp. 54-60.

Tenkanen, M. et al., "Two major xylanases of *Trichoderma reesei*", *Enzyme and Microbial Technology*, Jul. 1992, vol. 14, No. 7, pp. 566-574.

Notice of Reasons for Refusal dated Dec. 19, 2017, of counterpart Japanese Application No. 2017-519022, along with an English translation.

M. Hayn et al., "Separation and partial characterization of *Trichoderma reesei* cellulose by fast chromatofocusing," Journal of Chromatography A, vol. 329, 1985, pp. 379-387 (Abstract only).

Emilio Margolles-Clark et al., "Cloning of Genes Encoding α-L-Arabinofuranosidase and β-Xylosidase from *Trichoderma reesei* by Expression in *Saccharomyces cerevisiae*," Applied and Environmental Microbiology, vol. 62, No. 10, Oct. 1996, pp. 3840-3846.

Michael C. Herrmann et al., "The β-d-xylosidase of Trichoderma Reesei is a multifunctional β-d-xylan xylohydrolase," Biochemical Journal, vol. 321, No. 2, Jan 15, 1997, pp. 375-381 (Abstract only).

J. Xu et al., "A third xylanase from *Trichoderma reesei* PC-3-7," Applied Microbiology and Biotechnology, vol. 49, Issue 6, Jun. 1998, pp. 718-724 (Abstract only).

Elisabeth Würleitner et al., "Transcriptional Regulation of *xyn2* in *Hypocrea jecorina*," Eukaryotic Cell, vol. 2, No. 1, Feb. 2003, pp. 150-158.

Louise E. Rasmussen et al., "Mode of action and properties of the β-xylosidases from *Talaromyces emersonii* and *Trichoderma reesei*," Biotechnology and Bioengineering, vol. 94, No. 5, Jun. 28, 2006, pp. 869-876 (Abstract only).

Xinde Jiang et al., "New isolate of *Trichoderma viride* strain for enhanced cellulolytic enzyme complex production," Journal of Bioscience and Bioengineering, vol. 111, Issue 2, Feb. 2011, pp. 121-127 (Abstract only).

Henri Durand et al., "Genetic improvement of *Trichoderma reesei* for large scale cellulose production," Enzyme and Microbial Technology, vol. 10, Issue 6, Jun. 1988, pp. 341-346 (Abstract only).

Joseph Strauss et al., "CreI, the carbon catabolite repressor protein from *Trichoderma reesei*," FEBS Letters, vol. 376, Issue 1-2, 1995, pp. 103-107 (Abstact only).

Verena Seidl et al., "The *Hypocrea jecorina* (*Trichoderma reesei*) hypercellulolytic mutant RUT C30 lacks a 85 kb (29 gene-encoding) region of the wild-type genome," BMC Genomics, vol. 9:327, 2008.

Juliano de Oliveira Porciuncula et al., "Single Nucleotide Polymorphism Analysis of a *Trichoderma reesei* Hyper-Cellulolytic Mutant Developed in Japan," Bioscience, Biotechnology, and Biochemistry, vol. 77, Issue 3, 2013, pp. 534-543 (Abstract only).

Extended European Search Report dated Feb. 21, 2022, of counterpart European Patent Application No. 21205370.6.

R.M. Burke et al., "Carbohydrolase Production by the Ericoid Mycorrhizal Fungus *Hymenoscyphus ericae* Under Solid-State Fermentation Conditions," Mycological Research, Elsevier, Great Britain, vol. 101, No. 9, pp. 1135-1139, Sep. 1, 1997.

R. Tiwari et al., "Unwrapping the Hydrolytic System of the Phytopathogenic Fungus *Phoma exigua* by Secretome Analysis," Process Biochemistry, Elsevier, Great Britain, vol. 49, No. 10, pp. 1630-1636, Jul. 9, 2014.

\* cited by examiner

METHOD OF PRODUCING PROTEIN

TECHNICAL FIELD

This disclosure relates to a method of producing proteins using a fungus belonging to the genus *Trichoderma*.

BACKGROUND

Filamentous fungi are highly suitable for protein production because of their excellent protein secretion capacity. So far, filamentous fungi have been used in numerous protein production methods. Liquid culture of filamentous fungi, however, due to their aerobic nature, requires oxygen supply to culture media to keep the dissolved oxygen saturation of the culture media at or above a certain level during the culture. Since filamentous fungi have hyphae, the viscosity of the culture medium is increased as the culture progresses. Increased viscosity causes nonuniform distribution of oxygen and nutrients, which lowers the growth of the filamentous fungi and the productivity of proteins. Therefore, efficient protein production via culture of filamentous fungi requires, for example, agitation of the culture medium or increase of the oxygen supply.

Since an increase in the size of the culture tank decreases the oxygen-transfer coefficient, keeping the dissolved oxygen saturation at or above a certain level during the culture requires increasing the number of times of stirring and the amount of oxygen supply. However, increasing the number of stirring has a problem that it causes large shear damage to the fungal cells, and increasing the amount of oxygen supply has a problem that it requires greater energy input.

As a method of lowering the viscosity of the culture medium, JP 7-31467 A discloses a method in which a hyphal elongation inhibitor is add to the culture and the hyphal form is pelletized. WO 2012/027580 discloses a mutant strain of filamentous fungus in which secretion of proteins responsible for an increase in viscosity was inhibited.

On the other hand, to increase the amount of protein production using a filamentous fungus, methods comprising adding an inducer that induces protein production are known. For example, JP 2014-150745 A discloses a method comprising adding cellulose and, if needed, xylan or the like to the culture medium as an inducer to improve the productivity of cellulase as the protein.

As described above, the main problems in scaling up the culture of filamentous fungi have been the increase in energy used for stirring accompanying with the scaling up, and the amount of oxygen supply to the culture medium. Further, as will be described later in the examples, a problem was newly found that, when cellulose and xylan are added as inducers when culturing a fungus belonging the genus *Trichoderma* which is a filamentous fungus, the oxygen uptake rate is higher compared to the culture in which either cellulose or xylan is added alone. As the oxygen uptake rate increases, the dissolved oxygen saturation during culture further decreases.

SUMMARY

We found that, even when cellulose and xylan are used as inducers, using a fungus belonging to the genus *Trichoderma* in which the BXL1 gene encoding β-xylosidase has been disrupted decreases the oxygen uptake rate of the fungus belonging to the genus *Trichoderma* and suppresses the decrease in dissolved oxygen saturation.

We thus provide:

(1) A method of producing a protein using a fungus belonging to the genus *Trichoderma*, the method comprising culturing a fungus belonging to the genus *Trichoderma* whose BXL1 gene was disrupted, using a biomass containing cellulose and xylan as an inducer.

(2) The method according to (1), wherein the culturing is carried out adding the inducer to the culture medium to a concentration of at least 5% by weight (wt/wt).

(3) The method according to (1) or (2), wherein the inducer has a xylan content of 15 to 40% by weight.

(4) The method according to any one of (1) to (3), wherein the fungus belonging to the genus *Trichoderma* is *Trichoderma reesei*.

(5) The method according to (4), wherein the *Trichoderma reesei* is a strain in which carbon catabolite repression is removed.

(6) The method according to any one of (1) to (5), wherein the protein is a cellulase composition.

(7) The method according to (6), wherein β-xylosidase specific activity in the cellulase composition in terms of an enzyme activity for degrading p-nitrophenyl-β-D-xylopyranoside per 1 mg of protein in the cellulase composition is 0.006 U/mg protein or less; wherein cellobiohydrolase specific activity in terms of an enzyme activity for degrading p-nitrophenyl-β-D-lactopyranoside per 1 mg of protein in the cellulase is at least 0.1 U/mg protein; and wherein β-glucosidase specific activity in terms of an enzyme activity for degrading p-nitrophenyl-β-D-glucopyranoside per 1 mg of protein in the cellulase is at least 0.25 U/mg protein.

(8) The method according to (7), wherein the β-xylosidase specific activity is 0.002 U/mg protein or less; and wherein the β-glucosidase specific activity is at least 0.3 U/mg protein.

(9) A method of producing xylo-oligosaccharides, the method comprising hydrolyzing a biomass containing xylan and cellulose with the cellulase composition produced by the method according to any one of (6) to (8).

(10) A method of producing xylo-oligosaccharides and glucose, the method comprising hydrolyzing a biomass containing xylan and cellulose with the cellulase composition produced by the method according to any one of (6) to (8).

(11) A method of suppressing decrease in dissolved oxygen saturation when culturing a fungus belonging to the genus *Trichoderma* using a biomass containing cellulose and xylan as an inducer, the method comprising using a fungus belonging to the genus *Trichoderma* whose BXL1 gene was disrupted as the fungus belonging to the genus *Trichoderma*.

(12) A cellulase composition having the following characteristics (a) to (d):
  (a) β-xylosidase specific activity in the cellulase composition in terms of an enzyme activity for degrading p-nitrophenyl-β-D-xylopyranoside per 1 mg of protein in the cellulase composition is 0.006 U/mg protein or less;
  (b) cellobiohydrolase specific activity in terms of an enzyme activity for degrading p-nitrophenyl-β-D-lactopyranoside per 1 mg of protein in the cellulase composition is at least 0.1 U/mg protein;
  (c) β-glucosidase specific activity in terms of an enzyme activity for degrading p-nitrophenyl-β-D-glucopyranoside per 1 mg of protein in the cellulase composition is at least 0.25 U/mg protein; and
  (d) the protein concentration of the cellulase composition is 3 g/L or more.

(13) The cellulase composition according to (12), wherein the protein concentration is 9 g/L or more.

(14) The cellulase composition according to (12) or (13), wherein p-nitrophenyl-β-D-xylobioside-degrading activity per 1 mg of protein in the cellulase composition is at least 5 U/mg protein.

Using the BXL1 gene-disrupted fungus belonging to the genus *Trichoderma* enables suppression of the decrease in dissolved oxygen saturation even when xylose and cellulose are used as inducers.

DETAILED DESCRIPTION

"Inducer" refers to what acts to induce protein production by filamentous fungus and increases protein production. As the inducer, cellulose and so on are generally known. The inducer is a biomass containing cellulose and xylan. The biomass containing xylan and cellulose may be any plant-originated resources containing xylan and cellulose, and the plant includes, but not limited to, plants such as seed plants, pteridophytes, bryophytes, algae and water plants, pulp and waste building materials. Seed plants are divided into gymnosperms and angiosperms, both of which can be used preferably. Specific examples of gymnosperms include cycad, ginkgo, pine, fir, spruce and cryptomeria. Angiosperms are further divided into monocotyledons and dicotyledons. Specific examples of monocotyledons include bagasse, switchgrass, napier grass, Erianthus, corn stover, corncob, rice straw and wheat straw. Specific examples of dicotyledons used preferably include beet pulp, eucalyptus, oak and white birch.

These inducers may be treated to be suitable for addition to culture media. As specific treatment methods, known methods such as acid treatment, sulfuric acid treatment, dilute sulfuric acid treatment, alkali treatment, hydrothermal treatment, subcritical treatment, fine grinding, and steaming can be used.

The xylan content in the biomass as an inducer is not particularly limited, and is preferably at least 5% by weight, more preferably at least 10% by weight, still more preferably at least 15% by weight, still more preferably at least 15% by weight and 50% by weight or less, still more preferably at least 15% by weight and 40% by weight or less, still more preferably at least 15% by weight and 30% by weight or less, based on the solid weight of the biomass. The cellulose content is not particularly limited, and is preferably at least 50% by weight, more preferably at least 60% by weight, still more preferably at least 70% by weight, still more preferably at least 80% by weight, based on the solid weight of the biomass. The sum of the xylan content and the cellulose content never exceeds 100% by weight. The biomass may also contain components other than cellulose and xylan such as lignin and hemicellulose. The method of measuring the cellulose content and the xylan content in the biomass is not restricted, and the cellulose content and the xylan content specifically can be measured by the following method. First, the biomass sample to be subjected to the measurement is air-dried and pulverized with a Wiley mill or the like. After taking an appropriate amount of the sample and drying it at 105° C., the water content (wt %) is calculated from the weight loss. Thereafter, an appropriate amount (about 0.3 g) of the sample is weighed, 3 mL of 72% sulfuric acid is added, and the mixture is left to stand at 30° C. for 1 hour with intermittent stirring. The reaction liquid is mixed with 84 mL of purified water and then decomposed by heating in an autoclave at 120° C. for 1 hour. After the thermal decomposition, residues are filtered off from the decomposed solution. The filtrate and the residue washings are combined to the volume of 100 mL. The monosaccharides (such as glucose and xylose) are quantified by high performance liquid chromatography. The concentrations of the obtained monosaccharides (glucose, xylose) and the amount of decomposed sample (dry basis weight calculated from the water content) gives the content (cellulose, xylan) in the sample.

The added amount of the biomass used as an inducer is preferably at least 2% by weight as the final concentration based on the culture medium. Further, as the amount of the inducer added increases, the minimum dissolved oxygen saturation during culture described later becomes higher as compared to that with the parent strain, resulting in increase in the amount of protein produced, and thus the amount of the biomass added is more preferably at least 4% by weight, still more preferably at least 5% by weight, still more preferably at least 6% by weight, still more preferably at least 7% by weight, still more preferably at least 8% by weight, as the final concentration. When the BXL1 gene-disrupted fungus belonging to the genus *Trichoderma* is cultured and the obtained protein is used as a cellulase composition, increase in the amount of the biomass added as an inducer in the culturing leads to increase in the β-glucosidase and cellobiohydrolase activities, and decrease in the β-xylosidase activity. The amount of the biomass added to obtain a cellulase composition suitable for production of glucose and xylo-oligosaccharides is at least 4% by weight, more preferably at least 5% by weight, still more preferably at least 6% by weight, still more preferably at least 7% by weight, still more preferably at least 8% by weight, still more preferably at least 10% by weight, as the final concentration. The use of a filamentous fungus with low oxygen demand allows the amount of the inducer added to be increased, which gives increased amount of proteins produced by the filamentous fungus, thereby enabling efficient production of glucose and xylo-oligosaccharides through saccharification reaction. The inducer may be added at any time, but is preferably added before the start of the culturing. The amount of the inducer added is preferably 30% by weight or less, more preferably 20% by weight or less, because an excessive amount of inducer increases the energy for stirring.

The fungus belonging to the genus *Trichoderma* may be any fungus belonging to the genus *Trichoderma* as long as it has a capacity to produce proteins. A preferred fungus is *Trichoderma reesei*. Mutant strains originated from the genus *Trichoderma* and have been subjected to mutagenesis with a mutagen or ultraviolet irradiation to obtain improved protein productivity may also be used. Examples of the mutant strains include known mutant strains originated from *Trichoderma reesei*, that is, QM6a strain (NBRC 31326), QM9414 strain (NBRC31329), PC-3-7 strain (ATCC66589), QM9123 strain (NBRC31327), RutC-30 strain (ATCC56765), CL-847 strain (Enzyme. Microbiol. Technol. 10, 341-346 (1988)), MCG77 strain (Biotechnol. Bioeng. Symp. 8, 89 (1978)), MCG80 strain (Biotechnol. Bioeng. 12, 451-459 (1982)) and derivative strains thereof.

Preferred fungi belonging to the genus *Trichoderma* are those in which carbon catabolite repression is removed. The strains in which carbon catabolite repression is removed can produce more proteins because the production of proteins such as cellulase is elevated. More preferred strains are those in which carbon catabolite repression mediated by carbon catabolite repressor I is removed. The carbon catabolite repression mediated by carbon catabolite repressor I is removed by, for example, mutations in the carbon catabolite repressor I gene (cre1). It is known that CRE1 protein encoded by cre1 gene suppresses the expression of cellulase gene through catabolite repression by glucose (FEBS Lett., 376, 103-107, 1995). Therefore, when the cre1 gene is mutated, suppression of the expression of the cellulase gene is canceled and the production of cellulase is increased. Therefore, strains with mutations in cre1 gene are more suitable for producing proteins and cellulase compositions. A specific example of mutation in the cre1 gene includes a mutation in the cre1 gene of PC-3-7 strain (ATCC66589), in which A at position 232 is substituted with C, resulting in substitution of threonine at position 78 of the amino acid sequence with proline. It is known that this mutation elevates the production of cellulase (Biosci. Biotechnol. Biochem., 77 (3), 534-543,2013). It is known that in the RutC-30 strain (ATCC 56765), the cre1 gene is partly cleaved such that the carbon catabolite repression is removed (BMC Genomics., 9, 327, 2008). Strains having a mutation in the cre1 gene include strains having a frame shift by deletion or insertion of a base, a stop codon mutation by base substitution, or a base cleavage within the cre1 gene region, generated by a gene mutating agent, ultraviolet irradiation, or the like. Also included are strains in which all or part of the cre1 gene is removed or replaced with another gene by recombination or the like. Specifically, PC-3-7 strain (ATCC66589) and RutC-30 strain (ATCC56765), as well as strains that inherited the characteristics of PC-3-7 strain (ATCC66589) or RutC-30 strain (ATCC56765) are preferably used, and more preferably PC-3-7 strain (ATCC66589) and strains that inherited the characteristics of PC-3-7 strain (ATCC66589). The strains that inherited the characteristics of PC-3-7 (ATCC66589) or RutC-30 strain (ATCC56765) also include those that inherited the characteristics of PC-3-7 strain (ATCC66589) or RutC-30 strain (ATCC56765) and are newly mutated, and those that acquired an improved function by recombination.

Our method comprises culturing a fungus belonging to the genus *Trichoderma* whose BXL1 gene is disrupted. The BXL1 gene is involved in β-xylosidase activity. β-xylosidase is an enzyme that degrades xylobiose formed by β-1,4-linkage of xylose units, thereby producing xylose. The method of measuring β-xylosidase activity is not restricted and, for example, the β-xylosidase activity can be measured by using p-nitrophenyl-β-xylopyranoside (pNP-Xyl) as a substrate. Specifically, the measurement method is as follows. To 50 mM sodium acetate buffer solution adjusted to pH 5.0, which is the optimum pH for cellulase, p-nitrophenyl-β-D-xylopyranoside is dissolved to 1 mM, thereby obtaining a substrate solution. Then, 10 μL of an enzyme solution is added to 90 μL of the substrate solution and the obtained mixture is left to stand for reaction at 30° C. The reaction time, which is basically 30 minutes, is varied appropriately from 10 to 60 minutes depending on the enzyme activity. After the reaction, the reaction is stopped by adding 10 μL of sodium carbonate solution. The p-nitrophenol is quantified by measuring the absorbance at 405 nm. In the above reaction system, the amount of enzyme that produces 1 μmol of p-nitrophenol per minute is defined as 1 U. The activity is calculated as U per 1 mg of protein contained in the enzyme solution.

The method of measuring the protein concentration is not restricted, and the protein concentration may be measured by, for example, using a commercially available reagent for measuring protein concentration (Quick Start Bradford protein assay, Bio-Rad). Specifically, the measurement method is as follows. Five microliters of a diluted enzyme solution is added to 250 μL of the protein concentration measurement reagent which has been returned to room temperature. After leaving the mixture to stand at room temperature for 5 minutes to 40 minutes, the absorbance at 595 nm is measured using a microplate reader. Using BSA as a standard, the protein concentration is calculated based on the calibration curve.

"The BXL1 gene was disrupted" means the presence of a mutation, insertion, or deletion within the BXL1 gene, resulting in a decrease in β-xylosidase activity.

"A decrease in β-xylosidase activity" means that the β-xylosidase activity is decreased compared to that of the parent strain before the BXL1 gene is disrupted. The β-xylosidase activity is preferably reduced to ½ or less of that before the disruption of the BXL1 gene, more preferably to ⅕ or less, still more preferably ¹⁄₁₀ or less, still more preferably ¹⁄₂₀ or less, still more preferably ¹⁄₅₀ or less, particularly preferably ¹⁄₈₀ or less, most preferably ¹⁄₁₀₀ or less. The method of disrupting the BXL1 gene is not restricted and, for example, the BXL1 gene may be disrupted by introducing a frame shift mutation or inserting a stop codon into the BXL1 gene, using a gene mutation treatment with a gene mutating agent, ultraviolet irradiation or the like, or site-directed mutagenesis; or by removing or replacing with another gene the whole or a part of the BXL1 gene, using gene recombination (e.g., homologous recombination with another gene, see the Examples below). Since the BXL1 gene (Gene ID: 18483060) of fungi belonging to the genus *Trichoderma* is known, the gene can be easily disrupted by a conventional method.

The culture method of the fungus belonging to the genus *Trichoderma* will now be explained. The culture method is not restricted as long as proteins are produced, and a method commonly used to culture fungi belonging to the genus *Trichoderma* can be employed. As the carbon source used in the culture medium to be used, the above-mentioned biomass containing cellulose and xylan used as an inducer is preferably employed. As the nitrogen source to be used, for example, polypeptone, bouillon, CSL, soybean cake is employed. In addition, components required to produce the desired cellulase can be added to the culture medium. For the culture, various culture methods such as shaking culture, stirring culture, stirring and shaking culture, standing culture, and continuous culture can be employed, and among them, shaking culture and stirring culture are preferred. The culture temperature is usually 20° C. to 35° C., preferably 25° C. to 31° C.

The BXL1 gene-disrupted fungus belonging to the genus *Trichoderma* provides a higher protein concentration than the parent strain before the disruption and thus is more suitable for protein production. The increase in protein concentration may be any rate as long as the protein concentration is increased, and is preferably by 0.01% or more, more preferably by 0.02% or more, still more preferably by 0.04% or more, still preferably by 0.05% or more, still more preferably by 0.06% or more, still more preferably by 0.08% or more, still more preferably by 0.1% or more, still more preferably by 0.5% or more, still more preferably by 1% or more, still more preferably by 2% or more, still more preferably by 3% or more, still more preferably by 4% or more, still more preferably by 5% or more, still more preferably by 6% or more, still more preferably by 7% or more, still more preferably by 8% or more, still more preferably by 9% or more, still more preferably by 10% or more, still more preferably by 11% or more, still more preferably by 12% or more.

By disruption of the BXL1 gene of fungus belonging to the genus *Trichoderma*, the oxygen uptake rate of the fungus belonging to the genus *Trichoderma* when cellulose and xylan are added to the culture medium as inducers is decreased, and thus the decrease in the dissolved oxygen saturation during culture can be suppressed.

When the BXL1 gene-disrupted fungus belonging to the genus *Trichoderma* and the parent strain before the disruption are cultured under the same conditions with addition of cellulose and xylan as inducers to the culture medium, the BXL1 gene-disrupted strain shows remarkably decreased oxygen uptake rate (OUR) in the culture medium as compared with that with the parent strain before the disruption so that the dissolved oxygen saturation during culture is increased.

The oxygen uptake rate (mM/L/hr) refers to oxygen consumption rate per 1 L of culture medium per unit time at 24 hours after the start of culture. Specifically, the method of calculating the oxygen uptake rate comprises: carrying out culture while keeping the culture conditions constant; stopping the oxygen supply at 24 hours after the start of the culture; plotting the values of dissolved oxygen (DO values) (mg/L) every 10 seconds; and determining the slopes (A) (unit: mg/L/sec) at three or more plots where a logarithmic decrease occurs in the curve. Calculation of oxygen uptake rate is performed with Formula (1):

$$\text{Oxygen uptake rate(mM/L/hr)} = (-A) \times (1/32) \times 60 \times 60 \qquad (1).$$

Commercially available DO meters may be used for measurement of DO value. Any DO meter capable of accurately measuring DO value may be used. Examples of the DO meter include sealed DO electrode (ABLE Corporation) and dissolved oxygen sensor (Mettler Toledo). Zero and span calibrations are carried out previously for the DO meter. The zero calibration is carried out using 2% sodium sulfite solution. Span calibration comprises: carrying out aeration and agitation in the absence of fungal cells in actual culture conditions; waiting until the dissolved oxygen becomes saturated; confirming that the indicated value on the instrument is stable; and calibrating to saturated dissolved oxygen at the temperature. DO measurement with the culture tank pressurized also requires pressure correction. Hydrostatic pressure correction is further required when a large culture tank is used. The calculation for the correction is performed with Formula (2):

$$D = DO(1 + \alpha + \beta) \qquad (2)$$

D: corrected saturated dissolved oxygen
DO: saturated dissolved oxygen at 1 atm in pure water
α: gage pressure (kg/cm$^2$)
β: hydrostatic pressure (depth at the position of DO meter (m)/10).

The dissolved oxygen saturation is calculated as the ratio of dissolved oxygen during culture to saturated dissolved oxygen before the start of culture, which is taken as 100%. The dissolved oxygen (mg/L) represents a concentration of oxygen dissolved in water. The saturated dissolved oxygen refers to dissolved oxygen in a state in which the dissolved oxygen value becomes constant after performing aeration and agitation in the absence of fungal cells in actual culture conditions. When calculating the dissolved oxygen saturation, culture conditions such as aeration condition are not changed during the culture period. As oxygen demand decreases, dissolved oxygen saturation increases. The calculation of dissolved oxygen saturation is performed with Formula (3):

$$\text{Dissolved oxygen saturation (\%)} = (\text{dissolved oxygen during culture})/(\text{saturated dissolved oxygen before the start of culture}) \times 100 \qquad (3).$$

As used herein, "minimum saturation" refers to the lowest value of dissolved oxygen saturation as measured over time during culture. Higher minimum saturation means more suitable for scale-up.

When comparing oxygen uptake rates or dissolved oxygen saturations, it is desired to employ the same culture conditions such as culture medium, oxygen supply, agitation rate, temperature, culture volume and inoculum dose. The inoculum dose preferably is 10% (v/v) based on the main culture medium.

When the BXL1 gene-disrupted fungus belonging to the genus *Trichoderma* and the parent strain before the disruption are cultured under the same conditions, the BXL1 gene-disrupted strain provides a higher value of minimum saturation compared to the non-disrupted strain, preferably by at least 1%, more preferably by at least 2%, still more preferably by at least 4%, still more preferably by at least 5%, still preferably by at least 6%, still more preferably by at least 7%, still more preferably by at least 8%, still more preferably by at least 9%, still more preferably by at least 10%, still more preferably by at least 11%, still more preferably by at least 12%, still more preferably by at least 13%, still more preferably by at least 14%, particularly preferably by at least 15%.

We provide a method of producing a protein. Examples of the proteins include, but are not limited to, proteins used in the fields such as industrial, medical, agricultural, and foods. The proteins produced in filamentous fungi may be naturally occurring proteins originated from filamentous fungi, as well as heterologous proteins not originated from filamentous fungi. Specific examples of the proteins include cellulase, xylanase, pectinase, lyase, protease, kinase, amylase, pullulanase, lipase, esterase, perhydrolase, transferase, laccase, catalase, oxidase, reductase, chlorophyllase, hydrophobin, chymosin, carbonic anhydrase, thymidylate synthase, dihydrofolate reductase, tyrosine kinase, multidrug resistance protein, carmibal-P synthase, aspartate transcarbamylase, dihydroorotase, topoisomerase, ribonucleotide reductase, and antibodies, as well as other enzymes and non-enzyme proteins capable of being produced in filamentous fungi. The promoter to be used to express the target gene is not restricted, and the promoter used may preferably be a promoter of a cellobiohydrolase gene, an endoglucanase gene, or a xylanase gene with high expression level.

We further provide the use of the protein obtained by the production method as a cellulase composition. The cellulase composition is a mixture of various hydrolases that hydrolyze glycosidic linkages within β-1,4-glucan. Examples of hydrolases included in cellulase include cellobiohydrolase, xylanase, endoglucanase, β-glucosidase, β-xylosidase, arabinofuranosidase, xylanesterase, ferulic acid esterase, α-glucuronidase, chitosanase, chitinase, mannanase, mannosidase, α-galactosidase and β-galactosidase.

The cellulase composition obtained by culturing the BXL1 gene-disrupted fungus belonging to the genus *Trichoderma* provides a higher β-glucosidase activity than the cellulase composition obtained by culturing the parent strain before the disruption, thereby increasing glucose output during saccharification reaction, which is suitable for glucose. The increase in β-glucosidase activity may be any rate as long as the activity is increased, and is preferably by at least 0.5%, more preferably by at least 1%, still more preferably by at least 2%, still more preferably by at least 3%, still more preferably by at least 4%, still more preferably by at least 5%.

The β-xylosidase activity, β-glucosidase activity and cellobiohydrolase activity of the cellulase composition obtained are defined as follows. β-xylosidase can be quantified as described above, and the specific value is preferably not more than 0.040 U/mg protein, more preferably not more than 0.030 U/mg protein, still more preferably not more than 0.020 U/mg protein, still more preferably not more than 0.01 U/mg protein, still more preferably not more than 0.0080 U/mg protein, still more preferably not more than 0.0060 U/mg protein, still more preferably not more than 0.0050 U/mg protein, still more preferably not more than 0.0040 U/mg protein, still more preferably not more than 0.003 U/mg protein, still more preferably not more than 0.0020 U/mg protein.

The method of determining β-glucosidase activity is not restricted, and β-glucosidase activity may be determined by, for example, using p-nitrophenyl-β-glucopyranoside (pNP-gyl) as a substrate. Specifically, the activity is determined as follows. To 50 mM sodium acetate buffer solution adjusted to pH 5.0, which is the optimum pH for cellulase, 4-nitrophenyl-β-D-glucopyranoside is dissolved to 1 mM, thereby obtaining a substrate solution. Then, 10 μL of an enzyme solution is added to 90 μL of the substrate solution and the resulting mixture is left to stand for reaction at 30° C. The reaction time, which is basically 10 minutes, is varied appropriately from 10 to 60 minutes depending on the enzyme activity. After the reaction, the reaction is stopped by adding 10 μL of sodium carbonate solution. The p-nitrophenol is quantified by measuring the absorbance at 405 nm. In the above reaction system, the amount of enzyme that produces 1 μmol of p-nitrophenol per minute is defined as 1 U. The β-glucosidase activity value of the cellulase composition obtained is preferably at least 0.200 U/mg protein, more preferably at least 0.250 U/mg protein, still more preferably at least 0.280 U/mg protein, still more preferably at least 0.300 U/mg protein, still more preferably at least 0.320 U/mg protein.

The method of determining cellobiohydrolase activity is not restricted, and cellobiohydrolase activity may be determined by, for example, using p-nitrophenyl-β-lactopyranoside (pNP-lac) as a substrate. Specifically, the activity is determined as follows. To 50 mM sodium acetate buffer solution adjusted to pH 5.0, which is the optimum pH for cellulase, p-nitrophenyl-β-D-lactopyranoside is dissolved to 1 mM, thereby obtaining a substrate solution. Then, 10 μL of an enzyme solution is added to 90 μL of the substrate solution and the resulting mixture is left to stand for reaction at 30° C. The reaction time, which is basically 60 minutes, is varied appropriately from 10 to 60 minutes depending on the enzyme activity. After the reaction, the reaction is stopped by adding 10 μL of sodium carbonate solution. The 4-nitrophenol is quantified by measuring the absorbance at 405 nm. In the above reaction system, the amount of enzyme that produces 1 μmol of p-nitrophenol per minute is defined as 1 U. The cellobiohydrolase activity value of the cellulase composition obtained is preferably at least 0.100 U/mg protein, more preferably at least 0.120 U/mg protein, still more preferably at least 0.150 U/mg protein, still more preferably at least 0.160 U/mg protein.

The method of using the produced cellulase composition is not restricted, and the cellulase composition may preferably be used in the production of sugars, more preferably in the production of xylo-oligosaccharides, still more preferably in the production of xylo-oligosaccharides and glucose.

"Xylo-oligosaccharides" refer to those formed by β-glycosidic linkage of at least two or more xylose units. The degree of polymerization of xylo-oligosaccharides is not particularly limited, but preferred are from disaccharide (xylobiose) to hexasaccharide (xylohexaose) having high water solubility. Most preferred xylo-oligosaccharides include xylobiose, xylotriose, and xylotetraose which are easily utilized as a carbon source by enteric bacteria.

The cellulase composition is obtained by culturing the fungus belonging to the genus *Trichoderma* and used in saccharification reaction of a biomass. The method of preparing the cellulase composition is not restricted, and preferably the cells of the fungus belonging to the genus *Trichoderma* contained in the culture medium are removed, or do not grow to prevent consumption by the fungal cells, of glucose and xylo-oligosaccharides generated by saccharification reaction of cellulase composition and biomass. Examples of the method of removing the fungal cells include centrifugation and membrane separation. The treatment methods to prevent the fungal cells from growing include heat treatment, chemical treatment, acid/alkali treatment, and UV treatment.

The method of producing sugars using the cellulase composition obtained by culturing the fungus belonging to the genus *Trichoderma* is not restricted, and a biomass can be saccharified using the cellulase composition. As the biomass used for the saccharification reaction, the above-described biomass containing cellulose and xylan can be used. The biomass used for the saccharification reaction may be pretreated. The pretreatment method is not restricted and specifically known methods such as acid treatment, sulfuric acid treatment, dilute sulfuric acid treatment, alkali treatment, hydrothermal treatment, subcritical treatment, fine grinding treatment, and steaming treatment can be used. The reaction pH is not restricted and is preferably from about 3 to 7, more preferably from 4 to 6, still more preferably about 5. The reaction temperature is not restricted and is preferably from 40° C. to 70° C.

Through the saccharification reaction, xylo-oligosaccharides can be obtained. Alternatively, xylo-oligosaccharides and glucose can be obtained. In addition to xylo-oligosaccharides and glucose, for example, monosaccharides such as mannose, arabinose and galactose, and oligosaccharides such as cellobiose, cellotriose, cellotetraose, mannobiose and galactobiose produced by hydrolases contained in the cellulase composition may be contained.

The post-reaction solution produced from the saccharification reaction may contain, for example, inorganic salts, amino acids, proteins, and lignin as impurities. To remove these impurities, purification may be carried out. As the purification, known techniques such as ion exchange, membrane separation, crystallization, and demineralization can be applied.

A fraction containing monosaccharides (such as glucose and xylose) and a fraction containing xylo-oligosaccharides and so on produced are preferably separated in a post-process. Glucose is preferably used as a fermentation raw material in the production of chemical products, while xylo-oligosaccharides are preferably used for feeds, foods and cosmetic applications. Specific examples of the chemical products include alcohols such as ethanol, 1,3-propanediol, 1,4-butanediol and glycerol; organic acids such as acetic acid, lactic acid, pyruvic acid, succinic acid, malic acid, itaconic acid and citric acid; nucleosides such as inosine and guanosine; nucleotides such as inosinic acid and guanylic acid; and amine compounds such as cadaverine. On the other hand, only limited microorganisms can utilize xylose as a fermentation raw material. Furthermore, when a certain amount of xylose is given to pigs and so on as feed, about half is discharged as urine. Therefore, it is preferred to minimize the degradation from xylan and xylo-oligosaccharides to xylose to improve the yield of xylo-oligosaccharides.

The method of separating the monosaccharide fraction and xylo-oligosaccharides fraction is not restricted, and membrane separation is preferably used. At this time, less proportion of xylose decreases the amount of xylose contaminating a fraction of oligosaccharides such as xylo-oligosaccharides and cellobiose, which is advantageous in the membrane separation process.

We also provide a cellulase composition suitable for the production of xylo-oligosaccharides and glucose. The β-xylosidase activity, cellobiohydrolase activity, β-glucosidase activity and protein concentration of the cellulase composition are defined to have the following characteristics. The β-xylosidase activity can be determined as described above, and the value is specifically not more than 0.006 U/mg protein, more preferably not more than 0.005 U/mg protein, still more preferably not more than 0.004 U/mg protein, still more preferably not more than 0.003 U/mg protein, still more preferably not more than 0.002 U/mg protein, per 1 mg protein in the cellulase composition. The cellobiohydrolase activity can be determined as described above, and the value is specifically preferably at least 0.100 U/mg protein, more preferably at least 0.120 U/mg protein, still more preferably at least 0.150 U/mg protein, still more preferably at least 0.160 U/mg protein, per 1 mg protein in the cellulase composition. The 3-glucosidase activity can be determined as described above, and the value is specifically preferably at least 0.200 U/mg protein, more preferably at least 0.250 U/mg protein, still more preferably at least 0.280 U/mg protein, still more preferably at least 0.300 U/mg protein, still more preferably at least 0.320 U/mg protein, per 1 mg protein in the cellulase composition. The protein concentration can be measured as described above, and the value is preferably 3 g/L or more, more preferably 4 g/L or more, still more preferably 5 g/L or more, still more preferably 6 g/L or more, still more preferably 7 g/L or more, still more preferably 8 g/L or more, still more preferably 9 g/L or more.

By defining the p-nitrophenyl-β-D-xylobioside-degrading activity of the cellulase composition, a cellulase composition further suitable for the production of xylo-oligosaccharides and glucose is provided. The p-nitrophenyl-β-D-xylobioside-degrading activity can be determined by using p-nitrophenyl-β-D-xylobioside as a substrate. Specifically, the activity is determined as follows. To 50 mM sodium acetate buffer solution adjusted to pH 5.0, which is the optimum pH for cellulase, p-nitrophenyl-β-D-xylobioside is dissolved to 0.5 mM, thereby obtaining a substrate solution. Then, 10 μL of an enzyme solution is added to 90 μL of the substrate solution and the resulting mixture is left to stand for reaction at 30° C. The reaction time, which is basically 30 minutes, is varied appropriately from 10 to 60 minutes depending on the enzyme activity. After the reaction, the reaction is stopped by adding 10 μL of sodium carbonate solution. The p-nitrophenol is quantified by measuring the absorbance at 405 nm. In the above reaction system, the amount of enzyme that produces 1 μmol of p-nitrophenol per minute is defined as 1 U. The p-nitrophenyl-β-D-xylobioside-degrading activity value of the cellulase composition obtained is preferably at least 2 U/mg protein, more preferably at least 3 U/mg protein, still more preferably at least 4 U/mg protein, still more preferably at least 5 U/mg protein, still more preferably at least 6 U/mg protein.

As described above, production of proteins using the fungus belonging to the genus Trichoderma allows suppression of a decrease in dissolved oxygen saturation. Thus, we also provide a method of suppressing a decrease in dissolved oxygen saturation when culturing a fungus belonging to the genus Trichoderma using a biomass containing cellulose and xylan as an inducer, the method comprising using a BXL1 gene-disrupted fungus belonging to the genus Trichoderma as the fungus belonging to the genus Trichoderma.

EXAMPLES

Our methods, protein and compositions will now be described in detail with reference to examples, but is not limited thereto.

Reference Example 1 Method of Measuring Protein Concentration

A commercially available reagent for measuring protein concentration (Quick Start Bradford protein assay, Bio-Rad) was used. Five microliters of a diluted filamentous fungus-originated cellulase solution was added to 250 μL of the protein concentration measurement reagent which was previously returned to room temperature. After leaving the mixture to stand at room temperature for 5 minutes, the absorbance at 595 nm was measured using a microplate reader. Using BSA as a standard, the protein concentration was calculated based on the calibration curve.

Reference Example 2 Method of Determining β-Xylosidase Activity

To 90 μL of 50 mM acetate buffer containing 1 mM p-nitrophenyl-β-xylopyranoside (manufactured by Sigma-Aldrich Japan), was added 10 μL of enzyme dilution, and the mixture was allowed to react at 30° C. for 30 minutes. Then, 10 μL of 2 M sodium carbonate was added and mixed well to stop the reaction, and the increase in absorbance at 405 nm was determined. Release of 1 μmol of p-nitrophenol per minute was defined as 1 U of activity. For blanks, to 90 μL of 50 mM acetate buffer containing 1 mM p-nitrophenyl-β-xylopyranoside, was added 10 μL of 2 M sodium carbonate and mixed well. Then, 10 μL of enzyme dilution was added to the mixture and allowed to react at 30° C. for 30 minutes. Then, the increase in absorbance at 405 nm was determined. At this time, the enzyme solution was diluted such that the absorbance at 405 nm does not exceed 1. A calibration curve was prepared from the absorbance obtained as follows: adding 10 μL of a p-nitrophenol solution adjusted to a concentration of 0.1 mM, 0.2 mM, 1 mM, or 2 mM instead of the enzyme dilution; adding 10 μL of 2 M sodium carbonate and mixing well to develop color; and measuring the absorbance.

Reference Example 3 Method of Determining β-Glucosidase Activity

To 90 μL of 50 mM acetate buffer containing 1 mM p-nitrophenyl-β-glucopyranoside (manufactured by Sigma-Aldrich Japan), was added 10 μL of enzyme dilution, and the mixture was allowed to react at 30° C. for 10 minutes. Then, 10 μL of 2 M sodium carbonate was added and mixed well to stop the reaction, and the increase in absorbance at 405 nm was determined. Release of 1 μmol of p-nitrophenol per minute was defined as 1 U of activity. For blanks, to 90 μL of 50 mM acetate buffer containing 1 mM p-nitrophenyl-β-glucopyranoside, was added 10 μL of 2 M sodium carbonate and mixed well. Then, 10 μL of enzyme dilution was added to the mixture and allowed to react at 30° C. for 30 minutes. Then, the increase in absorbance at 405 nm was determined. At this time, the enzyme solution was diluted such that the absorbance at 405 nm does not exceed 1. A calibration curve was prepared from the absorbance obtained as follows: adding 10 μL of a p-nitrophenol solution adjusted to a concentration of 0.1 mM, 0.2 mM, 1 mM, or 2 mM instead of the enzyme dilution; adding 10 μL of 2 M sodium carbonate and mixing well to develop color; and measuring the absorbance.

Reference Example 4 Method of Determining Cellobiohydrolase Activity

To 90 μL of 50 mM acetate buffer containing 1 mM p-nitrophenyl-β-lactopyranoside (manufactured by Sigma-Aldrich Japan), was added 10 μL of enzyme dilution, and the mixture was allowed to react at 30° C. for 60 minutes. Then, 10 μL of 2 M sodium carbonate was added and mixed well to stop the reaction, and the increase in absorbance at 405 nm was determined. Release of 1 μmol of p-nitrophenol per minute was defined as 1 U of activity. For blanks, to 90 μL of 50 mM acetate buffer containing 1 mM p-nitrophenyl-β-lactopyranoside, was added 10 μL of 2 M sodium carbonate and mixed well. Then, 10 μL of enzyme dilution was added to the mixture and allowed to react at 30° C. for 30 minutes. Then, the increase in absorbance at 405 nm was determined. At this time, the enzyme solution was diluted such that the absorbance at 405 nm does not exceed 1. A calibration curve was prepared from the absorbance obtained as follows: adding 10 μL of a p-nitrophenol solution adjusted to a concentration of 0.1 mM, 0.2 mM, 1 mM, or 2 mM instead of the enzyme dilution; adding 10 μL of 2 M sodium carbonate and mixing well to develop color; and measuring the absorbance.

Reference Example 5 Method of Determining p-Nitrophenyl-β-D-Xylobioside-Degrading Activity To 90 μL of 50 mM acetate buffer containing 0.5 mM p-nitrophenyl-β-lactopyranoside, was added 10 μL of enzyme dilution, and the mixture was allowed to react at 50° C. for 30 minutes. Then, 10 μL of 2 M sodium carbonate was added and mixed well to stop the reaction, and the increase in absorbance at 405 nm was determined. Release of 1 μmol of p-nitrophenol per minute was defined as 1 U of activity. For blanks, to 90 μL of 50 mM acetate buffer containing 1 mM p-nitrophenyl-β-xylobioside, was added 10 μL of 2 M sodium carbonate and mixed well. Then, 10 μL of enzyme dilution was added to the mixture and allowed to react at 30° C. for 30 minutes. Then, the increase in absorbance at 405 nm was determined. At this time, the enzyme solution was diluted such that the absorbance at 405 nm does not exceed 1. A calibration curve was prepared from the absorbance obtained as follows: adding 10 μL of a p-nitrophenol solution adjusted to a concentration of 0.1 mM, 0.2 mM, 1 mM, or 2 mM instead of the enzyme dilution; adding 10 μL of 2 M sodium carbonate and mixing well to develop color; and measuring the absorbance.

Reference Example 6 Measurement of Sugar Concentrations

Quantitative analyses of xylo-oligosaccharide, glucose, and xylose were carried out using LaChrom Eite high performance liquid chromatography (HITACHI) under the following conditions.

The quantitative analyses were based on calibration curves prepared with standards of xylobiose, xylotriose, xylotetraose, xylopentaose and xylohexaose which are xylo-oligosaccharides, glucose and xylose. The xylo-oligosaccharides described in this example refer to xylo-oligosaccharides in which 2 to 6 xylose units are bound by β-glycosidic bonds.
Column: KS802, KS803 (Shodex)
Mobile phase: water
Detection method: RI
Flow rate: 0.5 mL/min
Temperature: 75° C.

Example 1 Preparation of BXL1 Gene-Disrupted Recombinant PC-3-7 Strain

PC-3-7/ΔBXL1 strain was prepared by substituting the ORF region of BXL1 gene with an acetamidase (AmdS) gene in PC-3-7 strain, and used as a BXL1 gene-disrupted strain in the following experiments. Specifically, a disruption plasmid was designed to add portions homologous to the introduction target site within the BXL1 locus to upstream and downstream of the DNA sequence containing the AmdS gene. AmdS gene containing the homologous regions was amplified by PCR using designed primers (SEQ ID NOs: 1 and 2). The obtained PCR fragments were transformed into PC-3-7 strain. The transformation was carried out by the standard PEG-mediated protoplast transformation method. More specifically, homologous recombination and transformation were carried out as described in Gene, 61, 165-176 (1987).

Comparative Example 1 Evaluation of Culture of PC-3-7 Using a Biomass Containing Cellulose and Xylan as an Inducer (8% Inducer Added)

Preculture
Spores of *Trichoderma reesei* strain PC-3-7 were suspended in physiological saline to $1.0 \times 10^7$/mL, and 2.5 mL of the obtained spore suspension was inoculated into 250 mL of a preculture medium having the composition shown in Table 1 placed in a 1 L baffled flask. The inoculated preculture medium was incubated at 28° C. and 160 rpm for 3 days. At this point of time, the fungal cell dry mass per culture was measured and found to be 11 mg/mL.

TABLE 1

| Components | per 1 L |
| --- | --- |
| D-glucose | 20 g |
| 5× Mandel's medium** | 200 mL |
| 10× ammonium tartrate | 100 mL |
| corn steep liquor | 15 g |
| trace elements* | 1 mL |
| Tween 80 | 0.5 mL |
| antifoaming agent (PE-M) | 1 mL |

*The trace element solution contains 0.3 g/L $H_3BO_3$, 1.3 g/L $(NH_4)_6Mo_7O_{24} \cdot 4H_2O$, 5 g/L $FeCl_3 \cdot 6H_2O$, 2 g/L $CuSO_4 \cdot 5H_2O$, 0.4 g/L $MnCl_2 \cdot 4H_2O$, and 10 g/L $ZnCl_2$.
**The Mandel's medium contains 7 g/L $(NH_4)_2SO_4$, 10 g/L $KH_2PO_4$, 3 g/L $CaCl_2$, and 3 g/L $MgSO_4 \cdot 7H_2O$.

Main Culture

Ten milliliters of the preculture of *Trichoderma reesei* strain PC-3-7 were each inoculated into 100 mL of the main culture medium (further containing 10 g of biomass) shown in Table 2 placed in a 200 mL mini jar. The inoculum was cultured at 28° C., 700 rpm, 1 vvm, pH5, for 5 days. The amount of the added biomass measured at the start of the culture was 8 wt % (wt/wt). For neutralization, 3.3% ammonia and 0.2 N sulfuric acid were used. Arbocel (registered trademark) (J. Rettenmaier & Sohne) containing cellulose and xylan was used as the biomass. SDOC-12F-L120 sealed DO electrode (ABLE Corporation) was used as a DO meter. No pressure was applied to the culture tank.

TABLE 2

| Components | per 1 L |
|---|---|
| biomass*** | 100 g |
| 5× Mandel's medium** | 200 mL |
| corn steep liquor | 25 g |
| trace element* | 1 mL |
| Tween 80 | 0.5 mL |
| antifoaming agent (PE-M) | 1 mL |

*The trace element solution contains 0.3 g/L $H_3BO_3$, 1.3 g/L $(NH_4)_6Mo_7O_{24} \cdot 4H_2O$, 5 g/L $FeCl_3 \cdot 6H_2O$, 2 g/L $CuSO_4 \cdot 5H_2O$, 0.4 g/L $MnCl_2 \cdot 4H_2O$, and 10 g/L $ZnCl_2$.
**The Mandel's medium contains 7 g/L $(NH_4)_2SO_4$, 10 g/L $KH_2PO_4$, 3 g/L $CaCl_2$, and 3 g/L $MgSO_4 \cdot 7H_2O$.
***Biomass is mixed with other components and added after dilution to a prescribed volume.

Culture Collection

Every other day from the start of culture, 500 µL of the culture was collected. The culture was centrifuged at 15,000×g, 4° C. for 10 minutes to obtain a supernatant. The supernatant was filtered through a 0.22 µm filter, and the filtrate was used as a culture supernatant to measure the protein concentration. For enzyme activity measurement, the culture supernatant on day 5 of culture was used (Table 3).

TABLE 3

| | Comparative Example 1 | Example 2 |
|---|---|---|
| strain used | PC-3-7 | PC-3-7/ΔBXL1 |
| β-xylosidase activity (U/mg protein) | 0.400 | 0.0018 |
| β-glucosidase activity (U/mg protein) | 0.300 | 0.330 |
| cellobiohydrolase activity (U/mg protein) | 0.158 | 0.159 |

Calculation of Oxygen Uptake Rate

Oxygen supply was stopped after 24 hours from the start of the culture, and the time course of the value of the dissolved oxygen amount (DO value) of the culture was measured every 10 seconds and plotted. Slopes at three or more plots where a logarithmic decrease occurs in the plotted curve were determined. From the slopes, oxygen uptake rate was determined (Table 4).

TABLE 4

| | Comparative Example 1 | Example 2 | Comparative Example 2 | Comparative Example 3 | Comparative Example 4 | Comparative Example 5 |
|---|---|---|---|---|---|---|
| strain used | PC-3-7 | PC-3-7/ΔBXL1 | PC-3-7 | PC-3-7/ΔBXL1 | PC-3-7 | PC-3-7/ΔBXL1 |
| inducer | cellulose and xylan | cellulose and xylan | xylan | xylan | cellulose | cellulose |
| oxygen uptake rate (mM/L/hr) | 6.88 | 2.48 | 3.11 | 9.20 | 3.89 | 2.84 |
| ratio of oxygen uptake rate (BXL1-disrupted strain/parent strain) | 100 | 36 | 100 | 296 | 100 | 73 |

Example 2 Evaluation of Culture of PC-3-7/ΔBXL1 Using a Biomass Containing Cellulose and Xylan as an Inducer (8% Inducer Added)

Enzyme activity (Table 3) and oxygen uptake rate (Table 4) were determined in the same manner as in Comparative Example 1 except that the strain used was the *Trichoderma reesei* PC-3-7/ΔBXL1 strain prepared in Example 1. At this point of time, the fungal cell dry mass per preculture was measured and found to be 11 mg/mL, which was the same as that of the parent (PC-3-7) strain. Determination of activity was carried out and revealed that the β-xylosidase activity decreased to 1/100 or less, while the β-glucosidase activity increased, as compared with the parent (PC-3-7) strain. Furthermore, it was revealed that in the PC-3-7/ΔBXL1 strain in Example 2, the oxygen uptake rate decreased to 36%, which was less than half compared to the result of the parent strain in Comparative Example 1. The biomass used as an inducer was Arbocel (trade name), which has a cellulose content of about 80% by weight and a xylan content of about 20% by weight.

Comparative Example 2 Evaluation of Culture of PC-3-7 Strain Using a Biomass Containing Xylan as an Inducer (8% Inducer Added)

Oxygen supply rate was calculated in the same manner as in Comparative Example 1 except that beech wood xylan (manufactured by Sigma-Aldrich) was used as the inducer (Table 4).

Comparative Example 3 Evaluation of Culture of PC-3-7/ΔBXL1 Strain Using a Biomass Containing Xylan as an Inducer (8% Inducer Added)

Oxygen uptake rate was calculated in the same manner as in Comparative Example 1 except that beech wood xylan (manufactured by Sigma-Aldrich) was used as the inducer and the strain used was *Trichoderma reesei* PC-3-7/ΔBXL1 strain (Table 4). When xylan was used as an inducer, the oxygen uptake rate of Comparative Example 3 increased to 296% compared to that of the parent (PC-3-7) strain (Comparative Example 2).

Comparative Example 4 Evaluation of Culture of PC-3-7 Using a Biomass Containing Cellulose as an Inducer (8% Inducer Added)

Oxygen uptake rate was calculated in the same manner as in Comparative Example 1 except that Cellulose microcrystalline (manufactured by Merck) which is microcrystalline cellulose was used as the inducer (Table 4).

Comparative Example 5 Evaluation of Culture of PC-3-7/ΔBXL1 Strain Using a Biomass Containing Cellulose as an Inducer (8% Inducer Added)

Oxygen uptake rates were determined in the same manner as in Comparative Example 1 except that Cellulose microcrystalline (manufactured by Merck) was used as the inducer and the strain used was *Trichoderma reesei* PC-3-7/ΔBXL1 strain (Table 4). When cellulose was used as an inducer, the oxygen uptake rate of Comparative Example 5 decreased to 73% compared to that of the parent (PC-3-7) strain (Comparative Example 4).

From the results of the cultures in Comparative Examples 1 to 5 and Example 2, we found that the parent strain, when cellulose and xylan were used as inducers, had remarkably increased oxygen uptake rate as compared with when cellulose or xylan alone was added as an inducer. Furthermore, we found that disruption of the BXL1 gene results in a significant reduction in oxygen uptake rate when cellulose and xylan are used as inducers. When cellulose and xylan, or cellulose alone were/was added as inducer(s), the protein concentrations of the obtained culture were almost the same. On the other hand, the protein concentration of the culture obtained when xylan alone was added as an inducer was very low, which was decreased to 1/10 or less of that obtained when cellulose and xylan were added as inducers, indicating that xylan alone is unsuitable for protein production.

Comparative Example 6 Evaluation of Culture of PC-3-7 Using Cellulose and Xylan as Inducers (8% Inducer Added)

Oxygen uptake rate was calculated in the same manner as in Comparative Example 1 except that 8.5 g of Cellulose microcrystalline (manufactured by Merck) which is microcrystalline cellulose and 1.5 g of beech wood xylan (manufactured by Sigma-Aldrich) were used as inducers to 100 mL of the main culture (Table 5). As a result, when using an inducer containing 15% by weight of xylan, the oxygen uptake rate was greatly increased compared to when using xylan alone (Comparative Example 2) or cellulose alone (Comparative Example 4) as an inducer.

Example 3 Evaluation of Culture of PC-3-7/ΔBXL1 Using Cellulose and Xylan as Inducers (8% Inducer Added)

Oxygen uptake rate was calculated in the same manner as in Comparative Example 1 except that 8.5 g of Cellulose microcrystalline (manufactured by Merck) which is microcrystalline cellulose and 1.5 g of beech wood xylan (manufactured by Sigma-Aldrich) were used as inducers to 100 mL of the main culture (Table 5). As a result, when using an inducer containing 15% by weight of xylan, the oxygen uptake rate of Example 3 was decreased to 56% compared to that of the parent (PC-3-7) strain (Comparative Example 6).

TABLE 5

| | Comparative Example 6 | Example 3 | Comparative Example 7 | Example 4 | Comparative Example 8 | Example 5 |
|---|---|---|---|---|---|---|
| strain used | PC-3-7 | PC-3-7/ΔBXL1 | PC-3-7 | PC-3-7/ΔBXL1 | PC-3-7 | PC-3-7/ΔBXL1 |
| weight percent of xylan | 15 | 15 | 30 | 30 | 40 | 40 |
| oxygen uptake rate (mM/L/hr) | 6.11 | 3.42 | 5.52 | 3.01 | 5.63 | 4.70 |
| ratio of oxygen uptake rate (BXL1-disrupted strain/parent strain) | 100 | 56 | 100 | 55 | 100 | 83 |
| protein concentration (g/L) | 9.00 | 10.15 | 8.50 | 9.55 | 5.90 | 6.50 |

Comparative Example 7 Evaluation of Culture of PC-3-7 Using Cellulose and Xylan as Inducers (8% Inducer Added)

Oxygen uptake rate was calculated in the same manner as in Comparative Example 1 except that 7 g of Cellulose microcrystalline (manufactured by Merck) which is microcrystalline cellulose and 3 g of beech wood xylan (manufactured by Sigma-Aldrich) were used as inducers to 100 mL of the main culture (Table 5). As a result, when using an inducer containing 30% by weight of xylan, the oxygen uptake rate was greatly increased compared to when using xylan alone (Comparative Example 2) or cellulose alone (Comparative Example 4) as an inducer.

Example 4 Evaluation of Culture of PC-3-7/ΔBXL1 Using Cellulose and Xylan as Inducers (8% Inducer Added)

Oxygen uptake rate was calculated in the same manner as in Comparative Example 1 except that 7 g of Cellulose microcrystalline (manufactured by Merck) which is microcrystalline cellulose and 3 g of beech wood xylan (manufactured by Sigma-Aldrich) were used as inducers to 100 mL of the main culture (Table 5). As a result, when using an inducer containing 30% by weight of xylan, the oxygen uptake rate of Example 4 was decreased to 55% compared to that of the parent (PC-3-7) strain (Comparative Example 7).

Comparative Example 8 Evaluation of Culture of PC-3-7 Using Cellulose and Xylan as Inducers (8% Inducer Added)

Oxygen uptake rate was calculated in the same manner as in Comparative Example 1 except that 6 g of Cellulose microcrystalline (manufactured by Merck) which is microcrystalline cellulose and 4 g of beech wood xylan (manufactured by Sigma-Aldrich) were used as inducers to 100 mL of the main culture (Table 6). As a result, when using an inducer containing 30% by weight of xylan, the oxygen uptake rate was greatly increased compared to when using xylan alone (Comparative Example 2) or cellulose alone (Comparative Example 4) as an inducer.

Example 5 Evaluation of Culture of PC-3-7/ΔBXL1 Using Cellulose and Xylan as Inducers (8% Inducer Added)

Oxygen uptake rate was calculated in the same manner as in Comparative Example 1 except that 6 g of Cellulose microcrystalline (manufactured by Merck) which is microcrystalline cellulose and 4 g of beech wood xylan (manufactured by Sigma-Aldrich) were used as inducers to 100 mL of the main culture (Table 6). As a result, when using an inducer containing 40% by weight of xylan, the oxygen uptake rate of Example 5 was decreased to 85% compared to that of the parent (PC-3-7) strain (Comparative Example 8).

From the results of the cultures in Comparative Examples 6 to 8 and Examples 3 to 5, we found that when cellulose and xylan were used as inducers, the oxygen uptake rate of the parent strain was remarkably increased as compared with when cellulose or xylan alone was added as an inducer. Furthermore, we found that disruption of the BXL1 gene resulted in a significant reduction in oxygen uptake rate compared to the parent strain, when an inducer in which cellulose and xylan were contained and the xylan content was 15 to 40% by weight was used.

Comparative Example 9 Evaluation of Culture of PC-3-7 Strain Using a Biomass Containing Cellulose and Xylan as an Inducer (5 L Jar) (8% Inducer Added)

Figure 1:
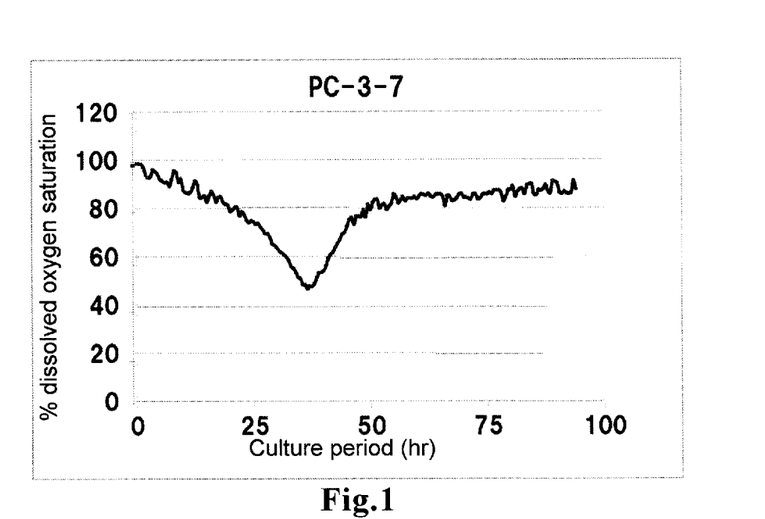
FIG. 1 shows the time-dependent change in dissolved oxygen saturation when culturing a fungus belonging to the genus *Trichoderma* in which BXL1 gene was not disrupted, as measured in a comparative example.

Since the effect of decreasing the oxygen uptake rate was confirmed with a 200 mL jar, culture on a larger 5 L scale was carried out and the change in DO value over the whole culture period was determined. Preculture was carried out in the same manner as in Comparative Example 1. In main culture, 250 mL of the preculture of *Trichoderma reesei* strain PC-3-7 were each inoculated into 2.5 L of the main culture medium shown in Table 2 placed in a 5 L mini jar. The inoculum was cultured at 28° C., 700 rpm, 1 vvm, pH5, for 5 days. For neutralization, 10% ammonia and 1 N sulfuric acid were used. Arbocel (registered trademark) (J. Rettenmaier & Sohne) was used as the biomass containing cellulose and xylan as inducers. The amount of the added biomass measured at the start of the culture was 8 wt % (wt/wt). After the start of the culture, the change in dissolved oxygen saturation was determined until the end of the culture (FIG. 1) and the minimum saturation was calculated (Table 6). The protein concentration was also measured 4 days after the start of culture (Table 6). SDOC-12F-L260 sealed DO electrode (ABLE Corporation) was used as a DO meter. No pressure was applied to the culture tank.

TABLE 6

| | Comparative Example 9 | Example 6 | Comparative Example 10 | Example 7 |
|---|---|---|---|---|
| strain used | PC-3-7 | PC-3-7/ΔBXL1 | PC-3-7 | PC-3-7/ΔBXL1 |
| inducer (%) | 8 | 8 | 2 | 2 |
| minimum saturation (%) | 45 | 60 | 83 | 87 |
| protein concentration (g/L) | 9.30 | 10.42 | 3.30 | 3.34 |

Example 6 Evaluation of Culture of PC-3-7/ΔBXL1 Using a Biomass Containing Cellulose and Xylan as an Inducer (5 L Jar) (8% Inducer Added)

Figure 2:
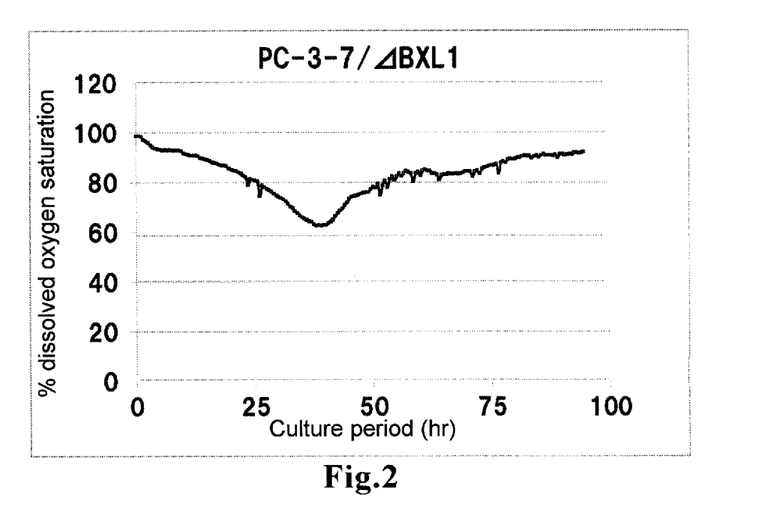
FIG. 2 shows the time-dependent change in dissolved oxygen saturation when culturing a fungus belonging to the genus *Trichoderma* in which BXL1 gene was disrupted, as measured in an example.

The change in dissolved oxygen saturation over the whole culture period was measured (FIG. 2), the minimum saturation was calculated (Table 6), and the protein concentration at 4 days after the start of culture was measured (Table 6) in the same manner as in Comparative Example 9 except that the strain used was *Trichoderma reesei* PC-3-7/ΔBXL1 strain. At this point of time, the fungal cell mass of preculture was the same as that of Comparative Example 9. As a result, the BXL1 gene-disrupted strain in Example 6 showed a lowered oxygen demand and a markedly increased minimum saturation compared to the results obtained by culturing the parent strain (PC-3-7) in Comparative Example 9. Further, the protein concentration was increased by 12% as compared with Comparative Example 9.

Comparative Example 10 Evaluation of Culture of PC-3-7 Strain Using a Biomass Containing Cellulose and Xylan as an Inducer (5 L Jar) (2% Inducer Added)

The minimum saturation was calculated and the protein concentration at 4 days after the start of culture was measured (Table 6) in the same manner as in Comparative Example 9 except that the main culture medium had the composition shown in Table 7. The amount of the added biomass measured at the start of the culture was 2 wt % (wt/wt).

TABLE 7

| Components | per 1 L |
|---|---|
| biomass | 20 g |
| 5× Mandel's medium** | 200 mL |
| corn steep liquor | 25 g |
| trace element* | 1 mL |
| Tween 80 | 0.5 mL |
| antifoaming agent (PE-M) | 1 mL |

*The trace element solution contains 0.3 g/L $H_3BO_3$, 1.3 g/L $(NH_4)_6Mo_7O_{24} \cdot 4H_2O$, 5 g/L $FeCl_3 \cdot 6H_2O$, 2 g/L $CuSO_4 \cdot 5H_2O$, 0.4 g/L $MnCl_2 \cdot 4H_2O$, and 10 g/L $ZnCl_2$.
**The Mandel's medium contains 7 g/L $(NH_4)_2SO_4$, 10 g/L $KH_2PO_4$, 3 g/L $CaCl_2$, and 3 g/L $MgSO_4 \cdot 7H_2O$.
***Biomass is mixed with other components and added after dilution to a prescribed volume.

Example 7 Evaluation of Culture of PC-3-7/ΔBXL1 Using a Biomass Containing Cellulose and Xylan as an Inducer (5 L Jar) (2% Inducer Added)

The minimum saturation was calculated and the protein concentration at 4 days after the start of culture was measured (Table 6) in the same manner as in Comparative Example 10 except that the strain used was *Trichoderma* reesei PC-3-7/ΔBXL1 strain. Compared to the results of Comparative Example 10, we found that, even when using 2% inducer, the minimum saturation increased, and the protein concentration was increased by 1% compared to the parent strain.

Comparative Example 11 Evaluation of Culture of PC-3-7 Strain Using a Biomass Containing Cellulose and Xylan as an Inducer (5 L Jar) (4% Inducer Added)

The minimum saturation was calculated and the protein concentration at 4 days after the start of culture was measured (Table 8) in the same manner as in Comparative Example 9 except that the amount of the biomass added to the main culture medium was changed to 46 g with respect to 1 L of the culture medium and other components had the composition shown in Table 7. The amount of the added biomass measured at the start of the culture was 4 wt % (wt/wt).

Example 8 Evaluation of Culture of PC-3-7/ΔBXL1 Using a Biomass Containing Cellulose and Xylan as an Inducer (5 L Jar) (4% Inducer Added)

The minimum saturation was calculated and the protein concentration at 4 days after the start of culture was measured (Table 8) in the same manner as in Comparative Example 11 except that the strain used was *Trichoderma reesei* PC-3-7/ΔBXL1 strain. Furthermore, the activity was determined (Table 10). Compared with the results of Comparative Example 11, we found that, even when using 4% inducer, the minimum saturation increased, and the protein concentration was increased by 1% as compared with the parent strain.

Comparative Example 12 Evaluation of Culture of PC-3-7 Strain Using a Biomass Containing Cellulose and Xylan as an Inducer (5 L Jar) (5% Inducer Added)

The minimum saturation was calculated and the protein concentration at 4 days after the start of culture was measured (Table 8) in the same manner as in Comparative Example 9 except that the amount of the biomass added to the main culture medium was changed to 58 g with respect to 1 L of the culture medium, and the other components had the composition shown in Table 7. The amount of the added biomass measured at the start of the culture was 5 wt % (wt/wt).

Example 9 Evaluation of Culture of PC-3-7/ΔBXL1 Using a Biomass Containing Cellulose and Xylan as an Inducer (5 L Jar) (5% Inducer Added)

The minimum saturation was calculated and the protein concentration at 4 days after the start of culture was measured (Table 8) in the same manner as in Comparative Example 12 except that the strain used was *Trichoderma reesei* PC-3-7/ΔBXL1 strain. Furthermore, the activity was determined (Table 10). Compared with the results of Comparative Example 12, we found that, even when using 5% inducer, the minimum saturation increased, and the protein concentration was increased by 8% compared to the parent strain.

Comparative Example 13 Evaluation of Culture of PC-3-7 Strain Using a Biomass Containing Cellulose and Xylan as an Inducer (5 L Jar) (6% Inducer Added)

The minimum saturation was calculated and the protein concentration at 4 days after the start of culture was measured (Table 9) in the same manner as in Comparative Example 9 except that the amount of the biomass added to the main culture medium was changed to 70 g with respect to 1 L of the culture medium, and the other components had the composition shown in Table 7. The amount of the added biomass measured at the start of the culture was 6 wt % (wt/wt).

Example 10 Evaluation of Culture of PC-3-7/ΔBXL1 Using a Biomass Containing Cellulose and Xylan as an Inducer (5 L Jar) (6% Inducer Added)

The minimum saturation was calculated and the protein concentration at 4 days after the start of culture was measured (Table 9) in the same manner as in Comparative Example 13 except that the strain used was *Trichoderma reesei* PC-3-7/ΔBXL1 strain. Furthermore, the activity was determined (Table 10). Compared with the results of Comparative Example 13, we found that, even when using 6% inducer, the minimum saturation increased, and the protein concentration was increased by 10% compared to the parent strain.

Comparative Example 14 Evaluation of Culture of PC-3-7 Strain Using a Biomass Containing Cellulose and Xylan as an Inducer (5 L Jar) (7% Inducer Added)

The minimum saturation was calculated and the protein concentration at 4 days after the start of culture was measured (Table 9) in the same manner as in Comparative Example 9 except that the amount of the biomass added to the main culture medium was changed to 83 g with respect to 1 L of the culture medium, and the other components had the composition shown in Table 7. The amount of the added biomass measured at the start of the culture was 7 wt % (wt/wt).

Example 11 Evaluation of Culture of PC-3-7/ΔBXL1 Using a Biomass Containing Cellulose and Xylan as an Inducer (5 L Jar) (7% Inducer Added)

The minimum saturation was calculated and the protein concentration at 4 days after the start of culture was measured (Table 9) in the same manner as in Comparative Example 14 except that the strain used was *Trichoderma reesei* PC-3-7/ΔBXL1 strain. Furthermore, the activity was determined (Table 10). Compared to the results of Comparative Example 14, we found that, even when using 7% inducer, the minimum saturation increased, and the protein concentration was increased by 11% compared to the parent strain.

Results obtained in Comparative Examples 9 to 14, and Examples 6 to 11 showed that when adding an inducer containing cellulose and xylan to and culturing the BXL1 gene-disrupted fungus belonging to the genus *Trichoderma*, the minimum saturation became higher than that with the parent strain as the amount of the inducer added increased.

Furthermore, we found that when the amount of the inducer added was 5% by weight or more, the protein concentration remarkably increased compared to the parent strain, demonstrating that the amount of the added inducer is more suitable for protein production.

TABLE 8

|  | Comparative Example 11 | Example 8 | Comparative Example 12 | Example 9 |
|---|---|---|---|---|
| strain used | PC-3-7 | PC-3-7/ΔBXL1 | PC-3-7 | PC-3-7/ΔBXL1 |
| inducer (%) | 4 | 4 | 5 | 5 |
| minimum saturation (%) | 80 | 85 | 70 | 77 |
| protein concentration (g/L) | 5.01 | 5.07 | 6.20 | 6.70 |

TABLE 9

|  | Comparative Example 13 | Example 10 | Comparative Example 14 | Example 11 |
|---|---|---|---|---|
| strain used | PC-3-7 | PC-3-7/ΔBXL1 | PC-3-7 | PC-3-7/ΔBXL1 |
| inducer (%) | 6 | 6 | 7 | 7 |
| minimum saturation (%) | 60 | 70 | 52 | 64 |
| protein concentration (g/L) | 7.10 | 7.86 | 7.90 | 8.80 |

TABLE 10

|  | Example 8 | Example 9 | Example 10 | Example 11 |
|---|---|---|---|---|
| inducer (%) | 4 | 5 | 6 | 7 |
| β-xylosidase activity (U/mg protein) | 0.005 | 0.003 | 0.002 | 0.0019 |
| β-glucosidase activity (U/mg protein) | 0.285 | 0.290 | 0.315 | 0.320 |
| cellobiohydrolase activity (U/mg protein) | 0.162 | 0.163 | 0.167 | 0.168 |
| p-nitrophenyl β-D-xylobioside-degrading activity (U/mg protein) | 4.20 | 4.40 | 5.01 | 5.20 |

Comparative Example 15 Evaluation of Saccharification of Bagasse Using a Cellulase Composition Obtained by Culturing PC-3-7 Strain Using a Biomass Containing Cellulose and Xylan as an Inducer (8% Inducer Added)

After centrifuging the culture after 4 days from the start of the culture obtained in Comparative Example 9, the supernatant was filtered through an ultrafilter membrane to remove fungal cells. The obtained filtrate was used in a saccharification reaction. A bagasse used in saccharification reaction had been subjected to an alkali treatment (pretreatment). The saccharification reaction was carried out as follows. After 50 mg by dry weight of the alkali-treated bagasse was placed in a 2 mL tube, pure water was added such that the solid content concentration of the bagasse at the start of reaction was 5% by weight, while pH was adjusted to 5.0 with diluted hydrochloric acid. To the pretreatment product with the adjusted pH, was added a cellulase composition (protein) to 8 mg/g-biomass, and then the reaction was initiated under reaction conditions of pH 5.0 and 50° C. using a heat block rotator. During the reaction, the pH was adjusted to 5 appropriately. After 8 hours, the reaction mixture was immersed in a water bath at 99° C. for 5 minutes to stop the reaction. The reaction liquid was centrifuged at 8,000×g for 5 minutes to obtain a supernatant. The supernatant was filtered through a 0.22 m filter, and the filtrate was used for analyses of xylo-oligosaccharides and glucose according to Reference Example 5. The results of xylo-oligosaccharides are shown in Table 11 and the results of glucose are shown in Table 12.

TABLE 11

|  | Comparative Example 15 | Example 12 |
|---|---|---|
| strain used | PC-3-7 | PC-3-7/ΔBXL1 |
| xylohexose (g/L) | 0.00 | 0.00 |
| xylopentose (g/L) | 0.00 | 0.00 |
| xylotetraose (g/L) | 0.77 | 0.90 |
| xylotriose (g/L) | 0.00 | 0.37 |
| xylobiose (g/L) | 0.00 | 5.68 |
| xylose (g/L) | 9.17 | 2.92 |
| total xylo-oligosaccharides (g/L) | 0.77 | 6.95 |
| xylose/(xylose + xylo-oligosaccharides) (%) | 92.3 | 29.6 |

TABLE 12

|  | Comparative Example 15 | Example 12 |
|---|---|---|
| strain used | PC-3-7 | PC-3-7/ΔBXL1 |
| glucose (g/L) | 9.19 | 10.3 |

Example 12 Evaluation of Saccharification of Bagasse Using a Cellulase Composition Obtained by Culturing PC-3-7/ΔBXL1 Strain Using a Biomass Containing Cellulose and Xylan as an Inducer (8% Inducer Added)

After centrifuging the culture after 4 days from the start of the culture obtained in Example 6, the supernatant was filtered through an ultrafilter membrane to remove fungal cells. A saccharification reaction was carried out in the same manner as in Comparative Example 15, and the resultant was used for analyses of xylo-oligosaccharides and glucose (Tables 11 and 12, respectively). As a result, the BXL1 gene-disrupted strain showed a markedly increased xylo-oligosaccharide yield compared to the parent strain (PC-3-7). Furthermore, we found that the yield of glucose was also increased compared to the parent strain.

Comparative Example 16 Evaluation of Saccharification of Bagasse Using a Cellulase Composition Obtained by Culturing PC-3-7 Strain Using a Biomass Containing Cellulose and Xylan as an Inducer (Xylan Content of 15%; 8% Inducer Added)

After centrifuging the culture after 4 days from the start of the culture obtained in Comparative Example 6, the supernatant was filtered through an ultrafilter membrane to remove fungal cells. A saccharification reaction was carried out in the same manner as in Comparative Example 15, and the resultant was used for analysis of glucose (Table 13).

Example 13 Evaluation of Saccharification of Bagasse Using a Cellulase Composition Obtained by Culturing PC-3-7/ΔBXL1 Strain Using a Biomass Containing Cellulose and Xylan as an Inducer (Xylan Content of 15%; 8% Inducer Added)

After centrifuging the culture after 4 days from the start of the culture obtained in Example 3, the supernatant was filtered through an ultrafilter membrane to remove fungal cells. A saccharification reaction was carried out in the same manner as in Comparative Example 15, and the resultant was used for analysis of glucose (Table 13).

Comparative Example 17 Evaluation of Saccharification of Bagasse Using a Cellulase Composition Obtained by Culturing PC-3-7 Strain Using a Biomass Containing Cellulose and Xylan as an Inducer (Xylan Content of 30%; 8% Inducer Added)

After centrifuging the culture after 4 days from the start of the culture obtained in Comparative Example 7, the supernatant was filtered through an ultrafilter membrane to remove fungal cells. A saccharification reaction was carried out in the same manner as in Comparative Example 15, and the resultant was used for analysis of glucose (Table 13).

Example 14 Evaluation of Saccharification of Bagasse Using a Cellulase Composition Obtained by Culturing PC-3-7/ΔBXL1 Strain Using a Biomass Containing Cellulose and Xylan as an Inducer (Xylan Content of 30%; 8% Inducer Added)

After centrifuging the culture after 4 days from the start of the culture obtained in Example 4, the supernatant was filtered through an ultrafilter membrane to remove fungal cells. A saccharification reaction was carried out in the same manner as in Comparative Example 15, and the resultant was used for analysis of glucose (Table 13).

Comparative Example 18 Evaluation of Saccharification of Bagasse Using a Cellulase Composition Obtained by Culturing PC-3-7 Strain Using a Biomass Containing Cellulose and Xylan as an Inducer (Xylan Content of 40%; 8% Inducer Added)

After centrifuging the culture after 4 days from the start of the culture obtained in Comparative Example 8, the supernatant was filtered through an ultrafilter membrane to remove fungal cells. A saccharification reaction was carried out in the same manner as in Comparative Example 15, and the resultant was used for analysis of glucose (Table 14).

Example 15 Evaluation of Saccharification of Bagasse Using a Cellulase Composition Obtained by Culturing PC-3-7/ΔBXL1 Strain Using a Biomass Containing Cellulose and Xylan as an Inducer (Xylan Content of 40%; 8% Inducer Added)

After centrifuging the culture after 4 days from the start of the culture obtained in Example 5, the supernatant was filtered through an ultrafilter membrane to remove fungal cells. A saccharification reaction was carried out in the same manner as in Comparative Example 15, and the resultant was used for analysis of glucose (Table 14).

Results obtained in Comparative Examples 15 to 18, and Examples 12 to 15 showed that when carrying out a saccharification reaction of a biomass containing cellulose and xylan using proteins obtained by culturing the BXL1 gene-disrupted fungus belonging to the genus *Trichoderma* with addition of an inducer containing cellulose and xylan as a cellulase composition, glucose yield was surprisingly increased compared to that with the parent strain.

TABLE 13

| | Comparative Example 16 | Example 13 | Comparative Example 17 | Example 14 |
|---|---|---|---|---|
| strain used | PC-3-7 | PC-3-7/ΔBXL1 | PC-3-7 | PC-3-7/ΔBXL1 |
| xylan content (%) | 15 | 15 | 30 | 30 |
| glucose (g/L) | 9.00 | 9.30 | 9.10 | 10.00 |

TABLE 14

| | Comparative Example 18 | Example 15 |
|---|---|---|
| strain used | PC-3-7 | PC-3-7/ΔBXL1 |
| xylan content (%) | 40 | 40 |
| glucose (g/L) | 8.40 | 8.80 |

Comparative Example 19 Evaluation of Saccharification of Bagasse Using a Cellulase Composition Obtained by Culturing PC-3-7/ΔBXL1 Strain Using a Biomass Containing Xylan as an Inducer (8% Inducer Added)

After centrifuging the culture after 4 days from the start of the culture obtained in Comparative Example 3, the supernatant was filtered through an ultrafilter membrane to remove fungal cells. After centrifuging the culture after 4 days from the start of the culture, the supernatant was filtered through an ultrafilter membrane to remove fungal cells. The obtained filtrate was measured for protein concentration (Table 16) and used in a saccharification reaction. A saccharification reaction was carried out in the same manner as in Comparative Example 15 except that the amount of the cellulase composition (protein) added was 2 mg/g-biomass and the reaction time was 24 hours, and the resultant was used for analysis of xylo-oligosaccharides (Table 15).

TABLE 15

| | Comparative Example 19 | Comparative Example 20 | Example 16 |
|---|---|---|---|
| inducer | Xylan | cellulose | cellulose and xylan |
| xylohexose (g/L) | 0.00 | 0.00 | 0.00 |
| xylopentose (g/L) | 0.24 | 0.22 | 0.25 |
| xylotetraose (g/L) | 1.05 | 1.09 | 1.07 |
| xylotriose (g/L) | 0.43 | 0.94 | 1.05 |
| xylobiose (g/L) | 4.88 | 3.66 | 4.36 |
| xylose (g/L) | 2.77 | 1.50 | 1.93 |
| xylo-oligosaccharides (g/L) | 6.60 | 5.91 | 6.73 |
| xylose/(xylose + xylo-oligosaccharides) (%) | 29.6 | 20.0 | 22.3 |

Comparative Example 20 Evaluation of Saccharification of Bagasse Using a Cellulase Composition Obtained by Culturing PC-3-7/ΔBXL1 Strain Using a Biomass Containing Cellulose as an Inducer (8% Inducer Added)

After centrifuging the culture after 4 days from the start of the culture obtained in Comparative Example 5, the supernatant was filtered through an ultrafilter membrane to remove fungal cells. The obtained filtrate was used in a saccharification reaction. A saccharification reaction was carried out in the same manner as in Comparative Example 19, and the resultant was used for analysis of xylo-oligosaccharides (Table 15).

Example 16 Evaluation of Saccharification of Bagasse Using a Cellulase Composition Obtained by Culturing PC-3-7/ΔBXL1 Strain Using a Biomass Containing Cellulose and Xylan as an Inducer (8% Inducer Added)

After centrifuging the culture after 4 days from the start of the culture obtained in Example 2, the supernatant was filtered through an ultrafilter membrane to remove fungal cells. The obtained filtrate was measured for protein concentration (Table 16) and then used in a saccharification reaction. A saccharification reaction was carried out in the same manner as in Comparative Example 19, and the resultant was used for analysis of xylo-oligosaccharides (Table 15). As a result, the highest yield of xylo-oligosaccharides was achieved in the culture to which cellulose and xylan were added as inducers. The second highest yield was obtained when xylan was used as an inducer. However, we found that the proportion of xylose/(xylose+xylo-oligosaccharides) was lower when cellulose and xylan were used as inducers, and membrane separation of xylo-oligosaccharides and xylose was easier. Culturing with addition of xylan as an inducer produced only about ⅒ proteins (cellulase composition) compared to when cellulose and xylan were used as inducers, thus requiring more culture during saccharification reaction.

The results in Tables 10 and 16 show that when the amount of the inducer added when culturing the BXL1 gene-disrupted fungus belonging to the genus *Trichoderma* was increased, the obtained cellulase composition had a decreased β-xylosidase activity and increased β-glucosidase and cellobiohydrolase activities, which shows that a cellulase composition more suitable for production of glucose and xylo-oligosaccharides is obtained. Especially, addition of at least 5% by weight of inducer resulted in decrease in the β-xylosidase activity to ½ or less compared to when 2% by weight was added, demonstrating that it is more suitable for production of glucose and xylo-oligosaccharides. More especially, addition of at least 6% by weight of inducer resulted in remarkable increase in the β-glucosidase activity compared to when 2% by weight was added, further demonstrating that it is suitable for production of glucose and xylo-oligosaccharides.

TABLE 16

| | Example 16 | Example 17 | Comparative Example 19 | Comparative Example 21 |
|---|---|---|---|---|
| inducer (%) | 8 | 2 | 8 | 2 |
| inducer type | cellulose and xylan | cellulose and xylan | xylan | xylan |
| β-xylosidase activity (U/mg protein) | 0.0018 | 0.006 | 0.009 | 0.018 |
| β-glucosidase activity (U/mg protein) | 0.330 | 0.280 | 0.140 | 0.180 |
| cellobiohydrolase activity (U/mg protein) | 0.170 | 0.160 | 0.066 | 0.071 |
| p-nitrophenyl β-D-xylobioside-degrading activity (U/mg protein) | 5.50 | 4.01 | 1.10 | 1.67 |
| protein concentration (g/L) | 10.43 | 3.06 | 0.76 | 0.63 |

Comparative Example 21 Evaluation of Saccharification of Bagasse Using a Cellulase Composition Obtained by Culturing PC-3-7/ΔBXL1 Strain Using a Biomass Containing Xylan as an Inducer (2% Inducer Added)

Culturing was carried out under the same conditions as in Comparative Example 1 except that the strain used was PC-3-7/ΔBXL1 strain, that the composition of the main culture was that shown in Table 7, and that beech wood xylan (manufactured by Sigma-Aldrich) was used as the biomass. After centrifuging the culture after 4 days from the start of the culture, the supernatant was filtered through an ultrafilter membrane to remove fungal cells. The obtained filtrate was measured for protein concentration (Table 16) and used in a saccharification reaction. A saccharification reaction was carried out in the same manner as in Comparative Example 19, and the resultant was used for analyses of xylo-oligosaccharides and glucose (Tables 17 and 18, respectively).

TABLE 17

| | Comparative Example 19 | Comparative Example 21 | Example 16 | Example 17 |
|---|---|---|---|---|
| inducer | xylan (8%) | xylan (2%) | cellulose and xylan (8%) | cellulose and xylan (2%) |
| xylohexose (g/L) | 0.00 | 0.00 | 0.00 | 0.00 |
| xylopentose (g/L) | 0.24 | 0.13 | 0.25 | 0.00 |
| xylotetraose (g/L) | 1.05 | 0.51 | 1.07 | 0.87 |
| xylotriose (g/L) | 0.43 | 0.36 | 1.05 | 0.49 |
| xylobiose (g/L) | 4.88 | 4.40 | 4.36 | 4.54 |
| xylose (g/L) | 2.77 | 2.92 | 1.93 | 1.93 |
| xylo-oligosaccharides (g/L) | 6.60 | 5.40 | 6.73 | 5.90 |
| xylose/(xylose + xylo-oligosaccharides) (%) | 29.6 | 35.1 | 22.3 | 24.6 |

TABLE 18

|  | Comparative Example 19 | Comparative Example 21 | Example 16 | Example 17 |
| --- | --- | --- | --- | --- |
| inducer | xylan (8%) | xylan (2%) | cellulose and xylan (8%) | cellulose and xylan (2%) |
| glucose (g/L) | 3.13 | 3.59 | 6.45 | 5.05 |

Example 17 Evaluation of Saccharification of Bagasse Using a Cellulase Composition Obtained by Culturing PC-3-7/ΔBXL1 Strain Using a Biomass Containing Cellulose and Xylan as an Inducer (2% Inducer Added)

Culturing was carried out under the same conditions as in Comparative Example 1 except that the strain used was PC-3-7/ΔBXL1 strain, and that the composition of the main culture was as shown in Table 7. After centrifuging the culture after 4 days from the start of the culture, the supernatant was filtered through an ultrafilter membrane to remove fungal cells. The obtained filtrate was measured for activities (Table 16). As a result, when 8% inducer was added, the β-xylosidase activity decreased, and β-glucosidase activity and p-nitrophenyl-β-D-xylobioside-degrading activity increased, as compared with those when 2% inducer added. The obtained filtrate was then used in a saccharification reaction. A saccharification reaction was carried out in the same manner as in Comparative Example 19, and the resultant was used for analyses of xylo-oligosaccharides and glucose (Tables 17 and 18, respectively). As a result, when the proportion of inducers added was the same, yields of xylo-oligosaccharides and glucose were increased more when using cellulose and xylan as inducers than when using xylan. In addition, the proportion of xylose/(xylose+xylo-oligosaccharides) was lower when using cellulose and xylan as inducers than when using xylan as an inducer. Further, when cellulose and xylan were used as inducers, yields of xylo-oligosaccharides and glucose were increased more, and also the proportion of xylose/(xylose+xylo-oligosaccha-rides) was lower, when the cellulase composition obtained by culturing with the addition of 8% inducer was used than the case of adding 2% inducer. These results show that a cellulase composition obtained by culturing with the addition of 8% cellulose and xylan as inducers is most suitable for production of xylo-oligosaccharides and glucose.

INDUSTRIAL APPLICABILITY

The use of the BXL1 gene-disrupted fungus belonging to the genus *Trichoderma* enables protein production under conditions with high dissolved oxygen saturation even when cellulose and xylan are added as inducers in the culture, thereby facilitating scale-up. Furthermore, the use of the protein obtained as a cellulase composition enables efficient production of xylo-oligosaccharides and glucose.

The invention claimed is:

1. A cellulase composition comprising hydrolases that hydrolyze glycosidic linkages and are obtained from a culture medium of BXL1 gene-disrupted *Trichoderma* having the following characteristics (a) to (d):
   (a) the cellulase composition has β-xylosidase specific activity in terms on an enzyme activity for degrading p-nitrophenyl-β-D-xylopyranoside per 1 mg of protein in said cellulase composition in an amount of 0.006 U/mg protein or less;
   (b) cellobiohydrolase specific activity in terms of an enzyme activity for degrading p-nitrophenyl-β-D-lactopyranoside per 1 mg of protein in said cellulase composition is at least 0.1 U/mg protein;
   (c) β-glucosidase specific activity in terms of an enzyme activity for degrading p-nitrophenyl-β-D-glucopyranoside per 1 mg of protein in said cellulase composition is at least 0.25 U/mg protein; and
   (d) the protein concentration of said cellulase composition is 3 g/L or more.

2. The cellulase composition according to claim 1, wherein said protein concentration is 9 g/L or more.

3. The cellulase composition according to claim 1, wherein p-nitrophenyl-β-D-xylobioside-degrading activity per 1 mg of protein in said cellulase composition is at least 5 U/mg protein.

4. The cellulase composition according to claim 2, wherein p-nitrophenyl-β-D-xylobioside-degrading activity per 1 mg of protein in said cellulase composition is at least 5 U/mg protein.

\* \* \* \* \*

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
cgatgaaaag caaaacacag                                        20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
ctgttcggta acgcatttct                                        20
```